(12) United States Patent
Torniainen et al.

(10) Patent No.: US 10,857,536 B2
(45) Date of Patent: *Dec. 8, 2020

(54) POLYMERASE CHAIN REACTION DEVICE

(71) Applicant: HEWLETT-PACKARD DEVELOPMENT COMPANY, L.P., Houston, TX (US)

(72) Inventors: Erik D Torniainen, Corvallis, OR (US); Alexander Govyadinov, Corvallis, OR (US); Pavel Kornilovich, Corvallis, OR (US); David P Markel, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 233 days.

This patent is subject to a terminal disclaimer.

(21) Appl. No.: 15/748,456

(22) PCT Filed: Jan. 8, 2016

(86) PCT No.: PCT/US2016/012699
§ 371 (c)(1),
(2) Date: Jan. 29, 2018

(87) PCT Pub. No.: WO2017/119902
PCT Pub. Date: Jul. 13, 2017

(65) Prior Publication Data
US 2018/0214866 A1 Aug. 2, 2018

(51) Int. Cl.
*B01L 3/00* (2006.01)
*C12M 3/06* (2006.01)
(Continued)

(52) U.S. Cl.
CPC ..... *B01L 3/50273* (2013.01); *B01L 3/502784* (2013.01); *B01L 7/52* (2013.01);
(Continued)

(58) Field of Classification Search
CPC .. B01L 3/50273; B01L 3/502784; B01L 7/52; B01L 2300/0896; B01L 2300/087;
(Continued)

(56) References Cited

U.S. PATENT DOCUMENTS

| 8,097,222 B2 | 1/2012 | Scurati | |
| 2002/0079219 A1* | 6/2002 | Zhao | B81B 7/007 |
| | | | 204/451 |

(Continued)

FOREIGN PATENT DOCUMENTS

| DE | 19717085 | 11/1998 |
| DE | 102010043030 | 5/2012 |

(Continued)

OTHER PUBLICATIONS

Fuchiwaki, "Study of a Liquid Plug-Flow Thermal Cycling Technique Using a Temperature Gradient-Based Actuator", Sensors 2014, 14, p. 20235-20244.

(Continued)

*Primary Examiner* — Michael L Hobbs
(74) *Attorney, Agent, or Firm* — Perry + Currier Inc

(57) ABSTRACT

Examples include polymerase chain reaction (PCR) devices. Example PCR devices comprise a fluid input, a fluid output, and a set of microfluidic channels that fluidly connect the fluid input and the fluid output. Each microfluidic channel comprises a reaction chamber, and examples further comprise at least one heating element, where the at least one heating element is positioned in the reaction chamber of each microfluidic channel. The at least one heating element is to heat fluid in the reaction chamber of each fluid channel, and the at least one heating element is to pump fluid to the reaction chamber and from the reaction chamber of each microfluidic channel.

12 Claims, 12 Drawing Sheets

(51) Int. Cl.
*C12M 1/34* (2006.01)
*B01L 7/00* (2006.01)
*C12Q 1/686* (2018.01)

(52) U.S. Cl.
CPC ............ *C12M 23/16* (2013.01); *C12M 41/12* (2013.01); *B01L 2300/087* (2013.01); *B01L 2300/0861* (2013.01); *B01L 2300/0864* (2013.01); *B01L 2300/0896* (2013.01); *B01L 2300/1827* (2013.01); *B01L 2400/0442* (2013.01); *B01L 2400/0481* (2013.01); *C12Q 1/686* (2013.01)

(58) Field of Classification Search
CPC ..... B01L 2300/0864; B01L 2300/0861; B01L 2300/1827; B01L 2400/0481; B01L 2400/0442; C12M 41/12; C12M 23/16; C12Q 1/686
See application file for complete search history.

(56) References Cited

U.S. PATENT DOCUMENTS

| | | | |
|---|---|---|---|
| 2003/0008308 A1* | 1/2003 | Enzelberger | B01F 5/102 435/6.19 |
| 2003/0138829 A1* | 7/2003 | Unger | B01L 3/502707 506/7 |
| 2005/0202489 A1 | 9/2005 | Cho et al. | |
| 2005/0265899 A1 | 12/2005 | Imamura et al. | |
| 2008/0210319 A1 | 9/2008 | Unger et al. | |
| 2008/0220414 A1 | 9/2008 | Jensen et al. | |
| 2009/0185955 A1 | 7/2009 | Nellissen | |
| 2012/0052560 A1 | 3/2012 | Knight et al. | |
| 2012/0141999 A1 | 6/2012 | Park et al. | |
| 2012/0244604 A1* | 9/2012 | Kornilovich | B01L 3/50273 435/286.1 |
| 2014/0051159 A1 | 2/2014 | Bergstedt et al. | |
| 2015/0151301 A1 | 6/2015 | Fiorini et al. | |

FOREIGN PATENT DOCUMENTS

| | | |
|---|---|---|
| EP | 2749349 | 7/2014 |
| JP | 2008151772 | 7/2008 |
| KR | 20110092239 A | 8/2011 |
| WO | WO-9736681 | 10/1997 |
| WO | WO-0107159 | 2/2001 |
| WO | WO-2014148800 | 9/2014 |

OTHER PUBLICATIONS

Park, "Integration of Sample Pretreatment, μPCR, and Detection . . . ", Oct. 2014, p. 1655-1668, vol. 181, Issue 13, http://link.springer.com/article/10.1007%2Fs00604-013-1128-y.

* cited by examiner

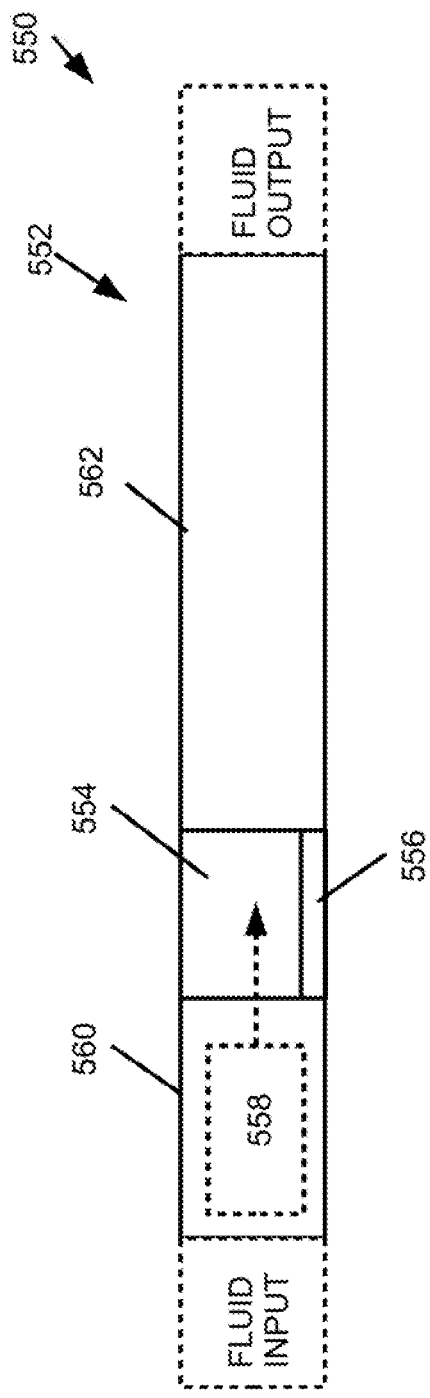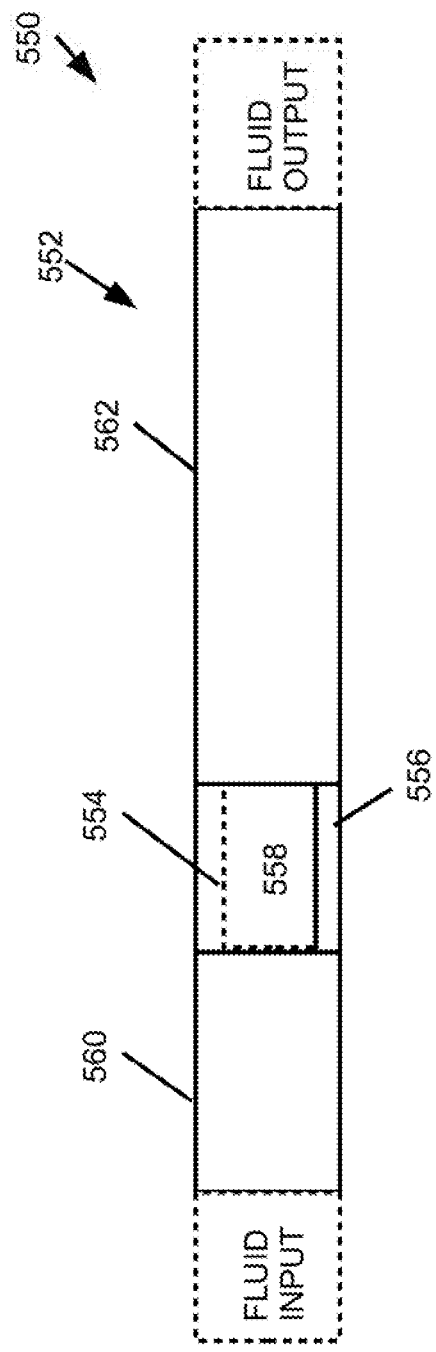

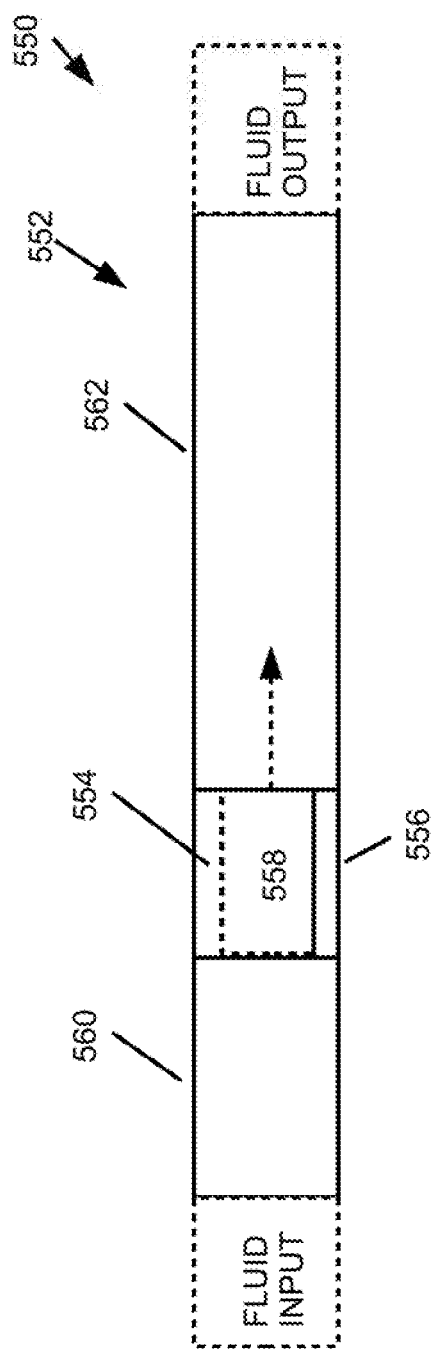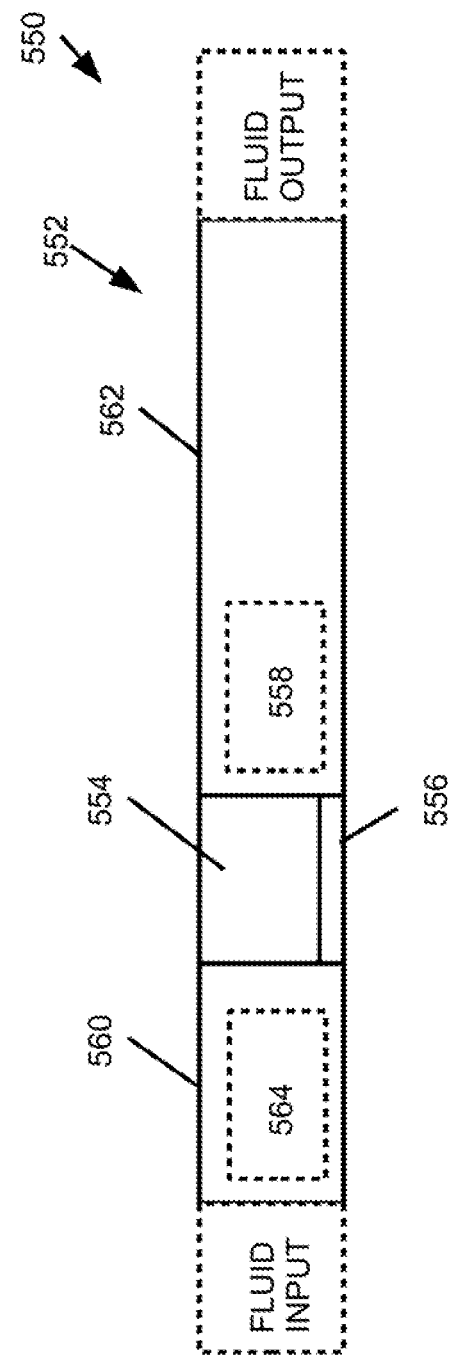

POLYMERASE CHAIN REACTION DEVICE

BACKGROUND

Polymerase chain reaction (PCR) is a process by which a deoxyribonucleic acid (DNA) molecule may be amplified (replicated) into thousands, millions, or billions of copies of the molecule. In a PCR process, a sample DNA template, primer, polymerase, reaction buffer, and deoxynucleotide (dNTP) may be included in a PCR mixture. The PCR mixture may be cycled through various temperatures in a PCR process such that the included DNA template is amplified.

DRAWINGS

Figure 1:
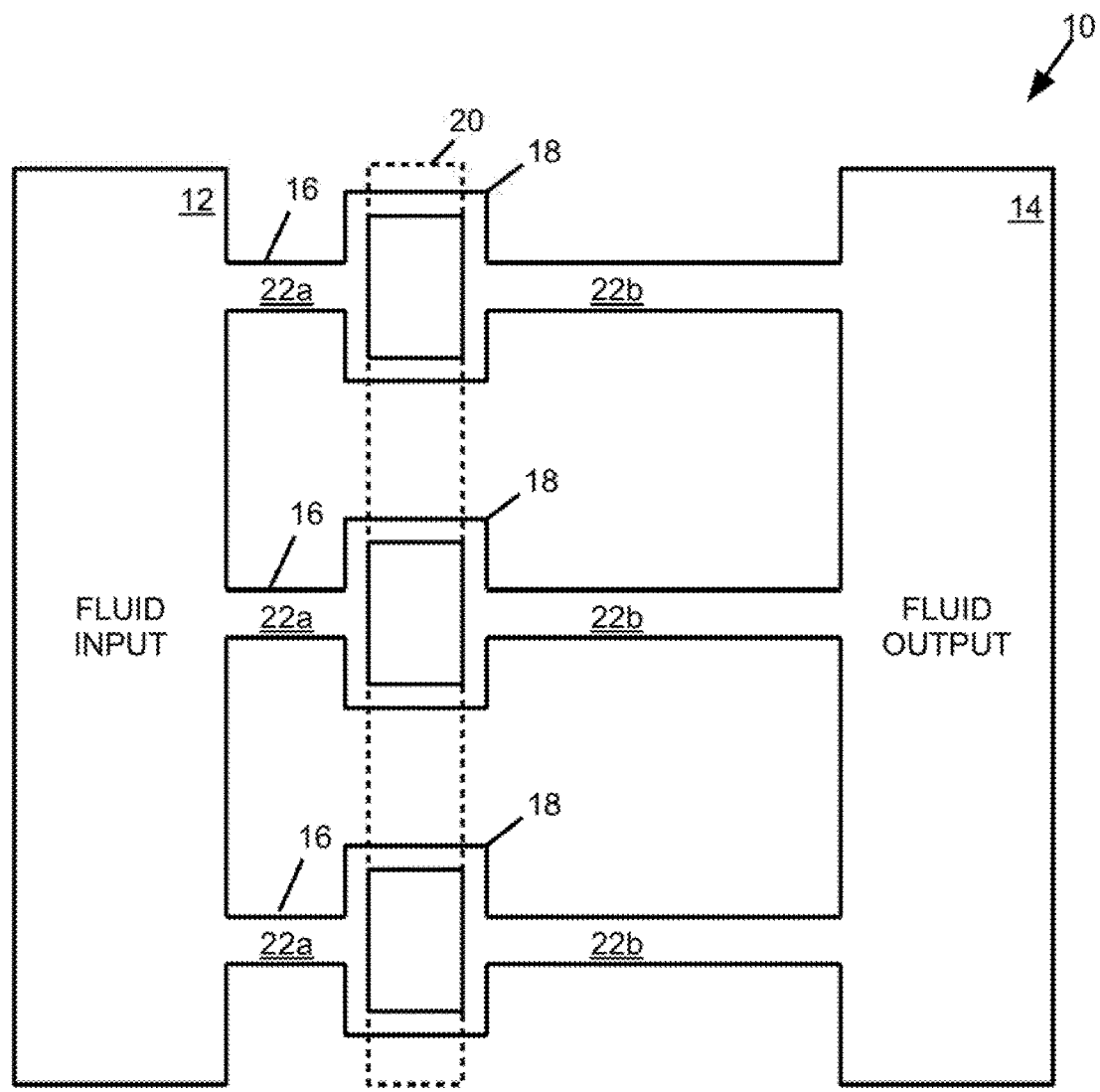

FIG. 1 provides a block diagram of some components of an example polymerase chain reaction device.

Figure 2:
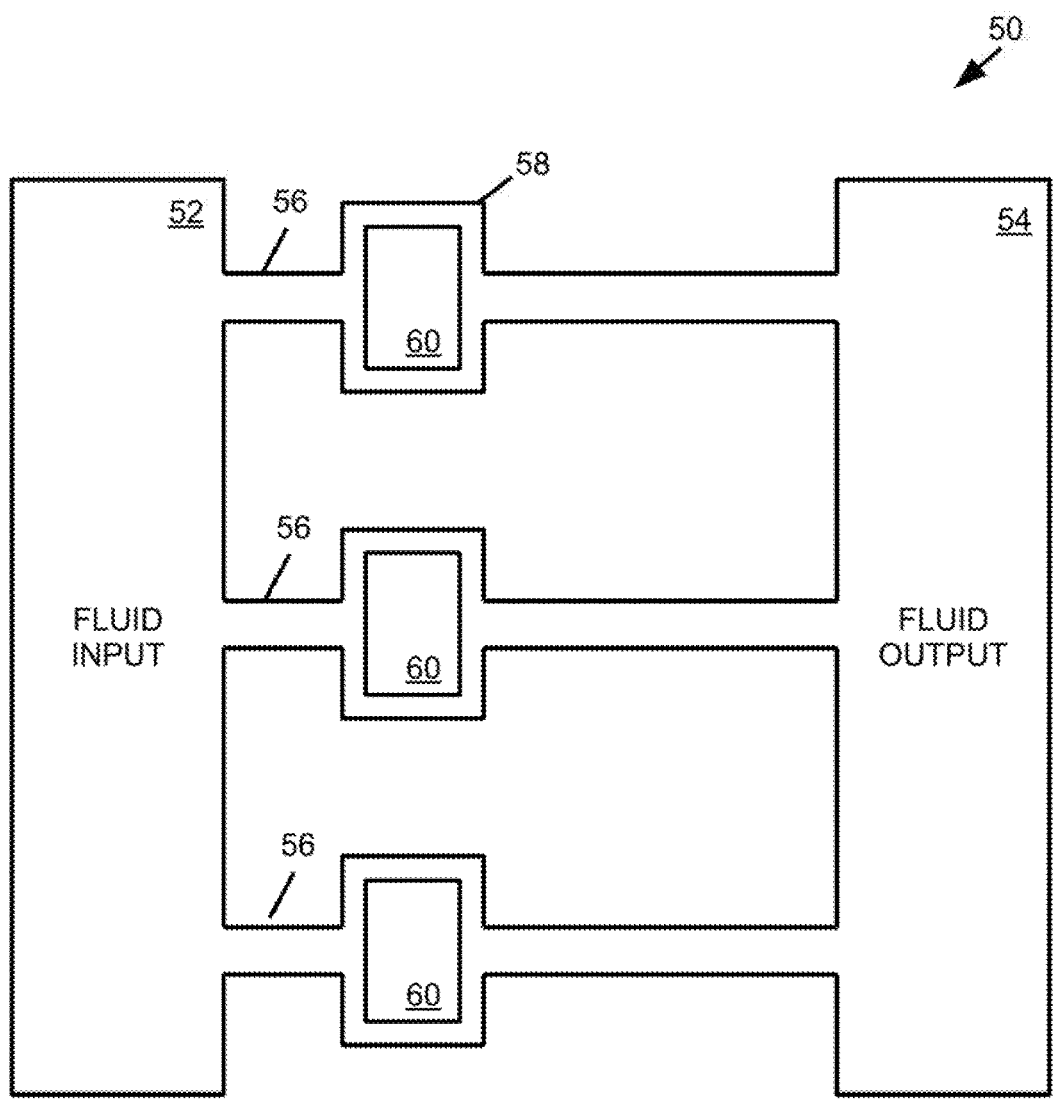

FIG. 2 provides a block diagram of some components of an example polymerase chain reaction device.

Figure 3:
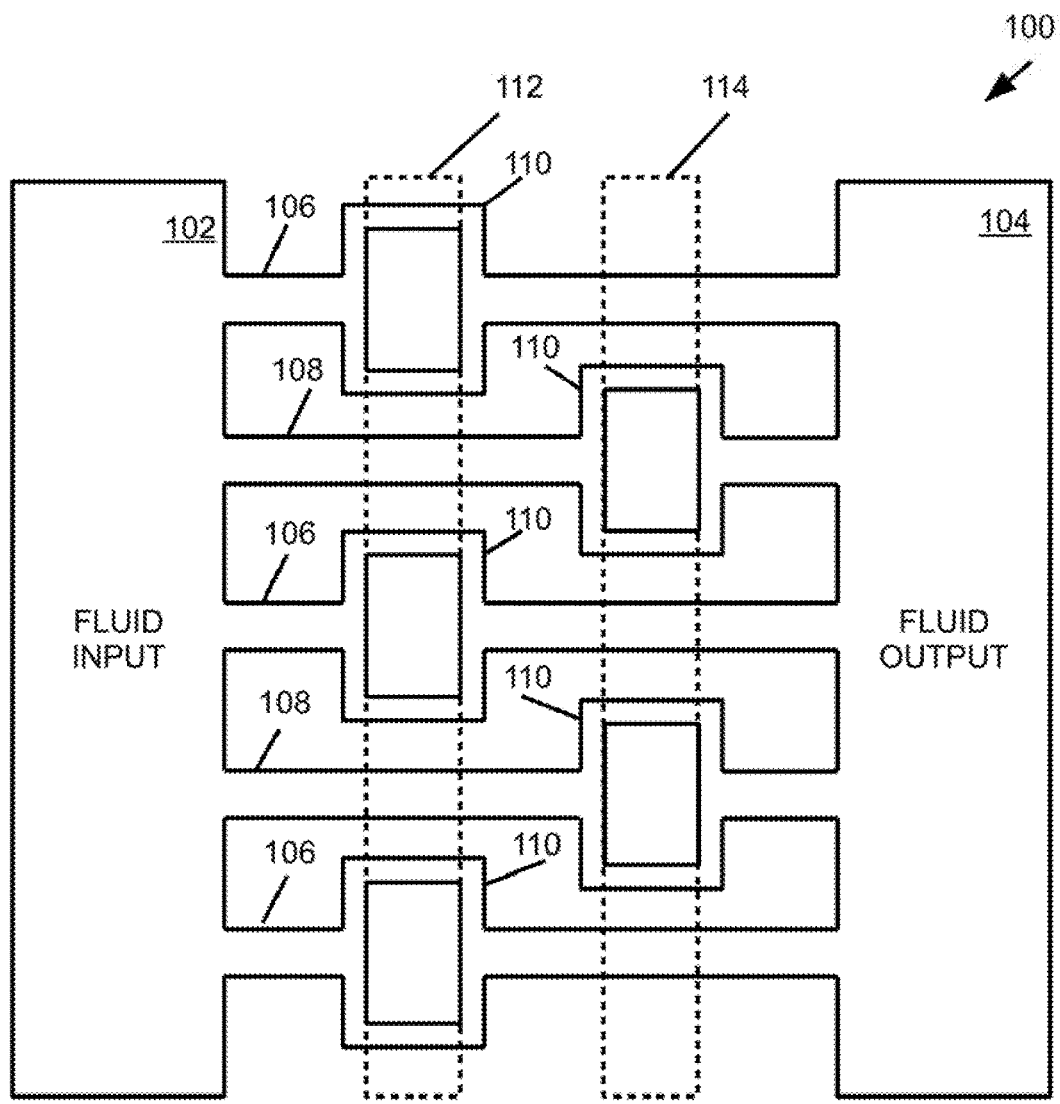

FIG. 3 provides a block diagram of some components of an example polymerase chain reaction device.

Figure 4:
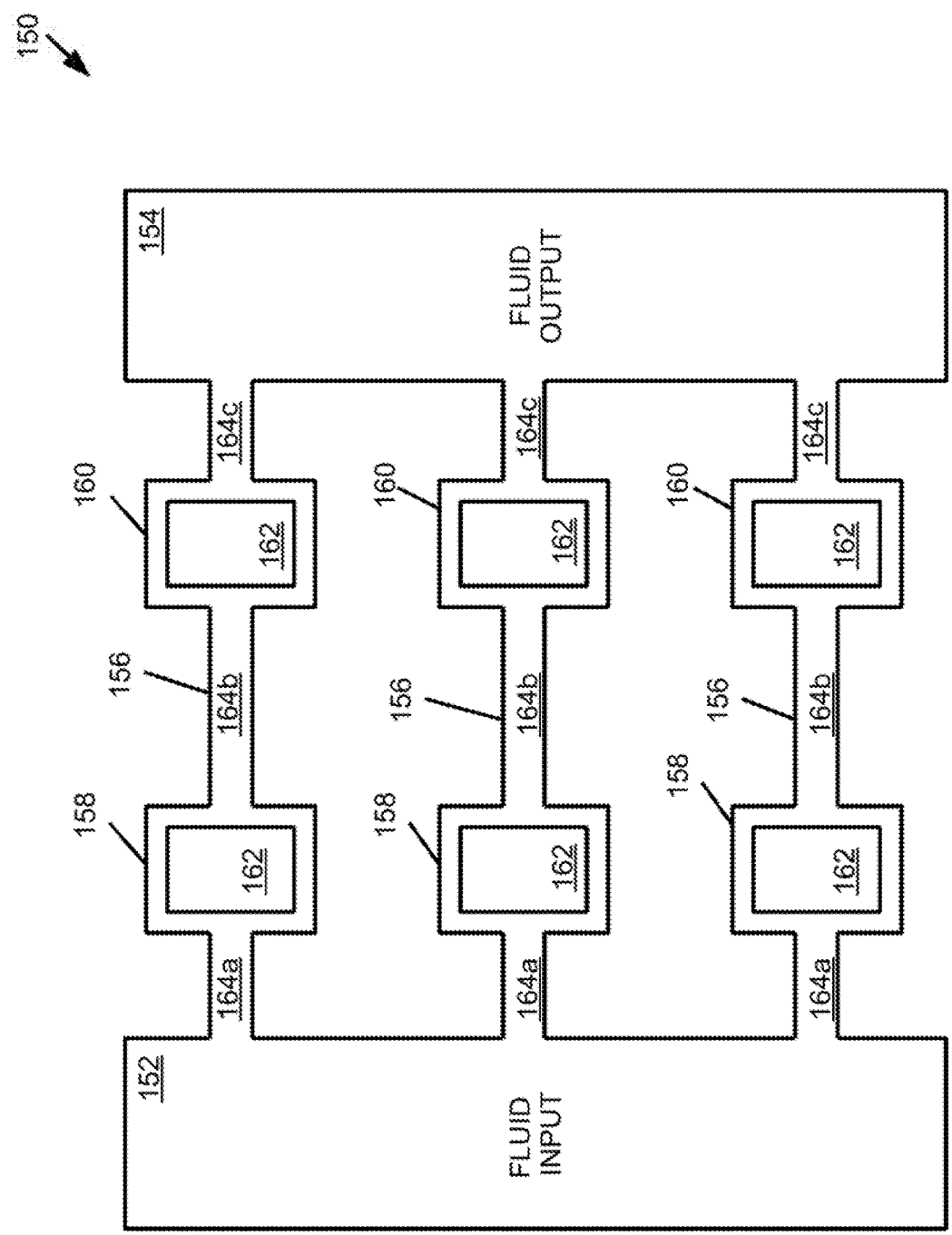

FIG. 4 provides a block diagram of some components of an example polymerase chain reaction device.

Figure 5:
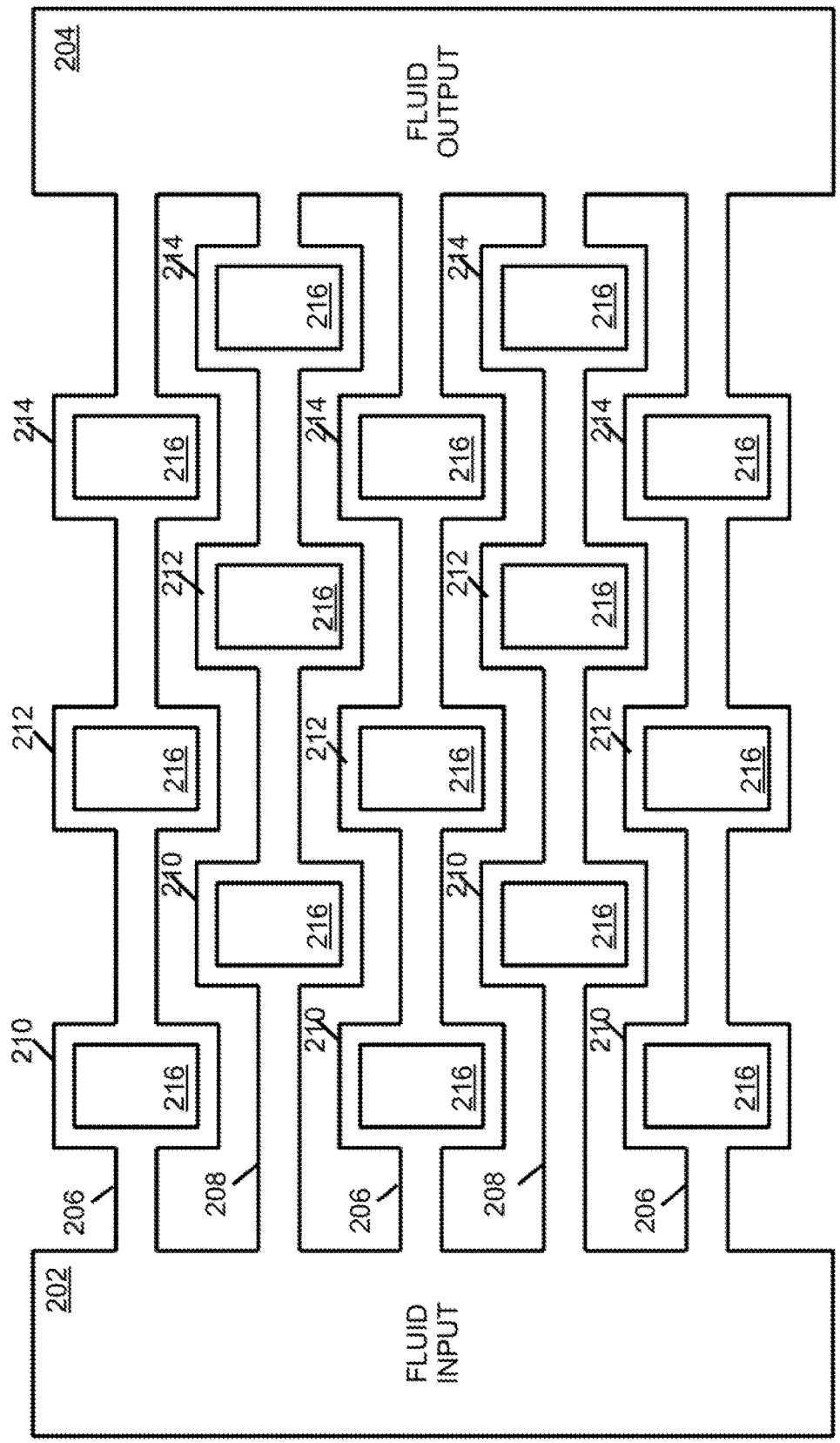

FIG. 5 provides a block diagram of some components of an example polymerase chain reaction device.

Figure 6:
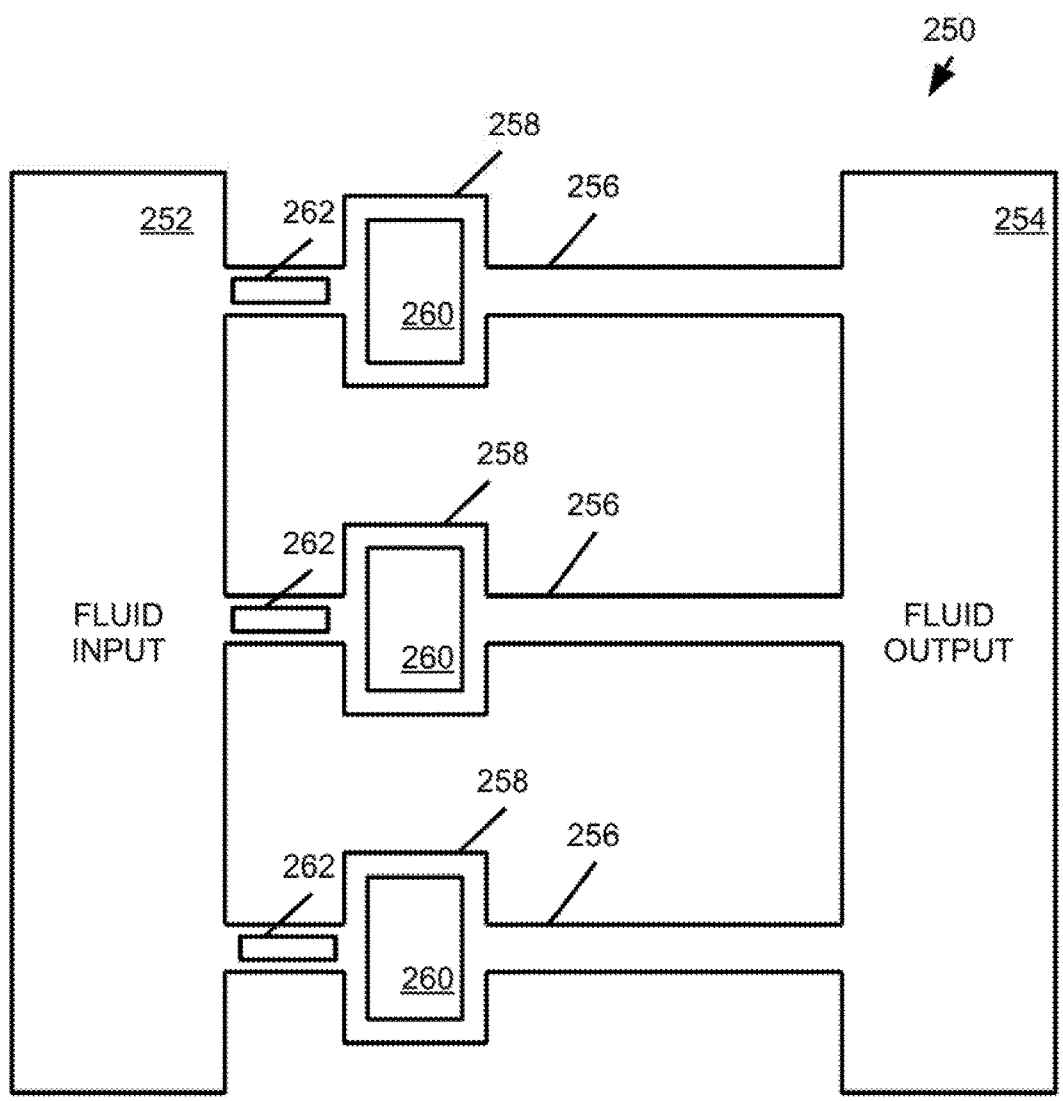

FIG. 6 provides a block diagram of some components of an example polymerase chain reaction device.

Figure 7:
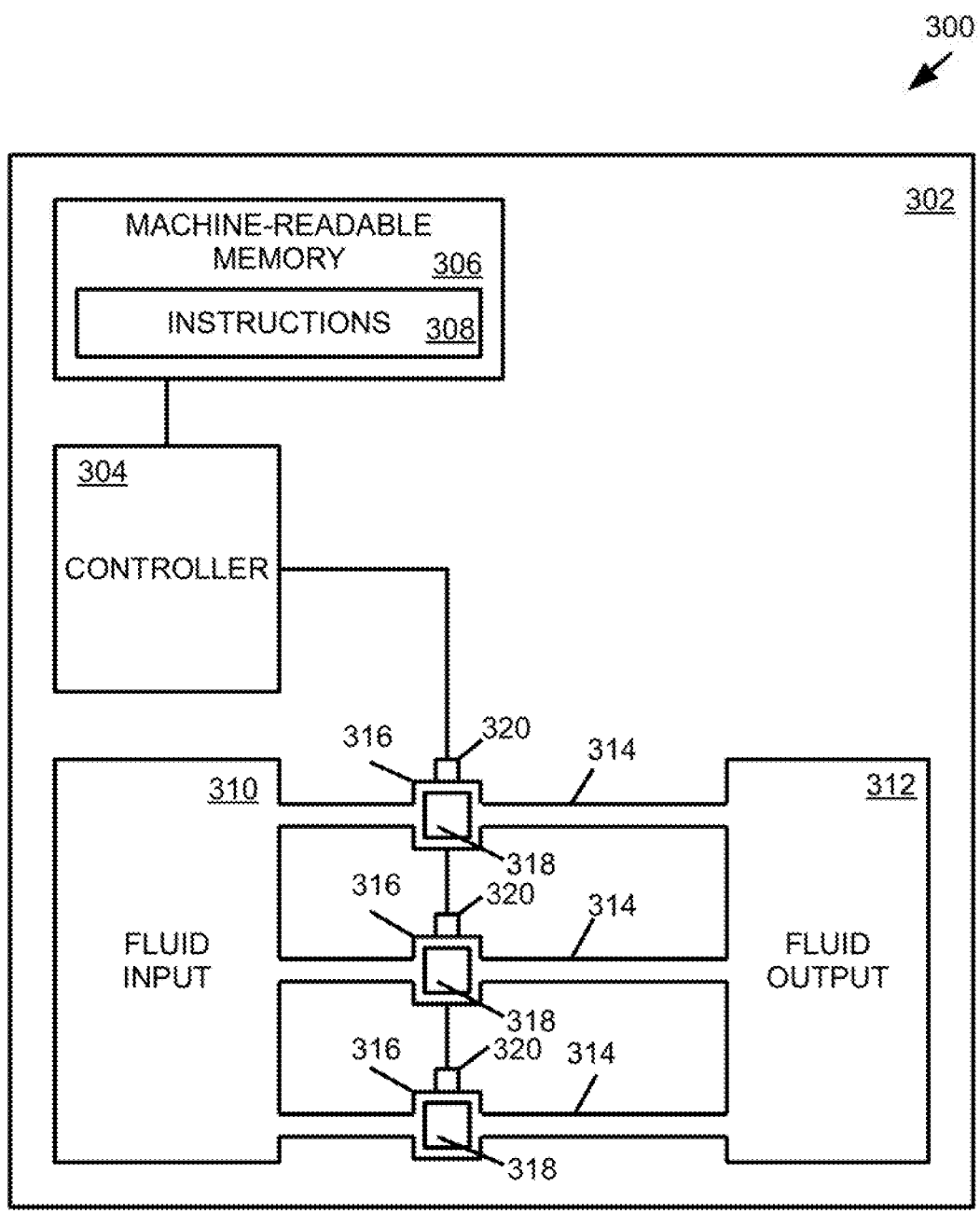

FIG. 7 provides a block diagram of some components of an example polymerase chain reaction device.

Figure 8:
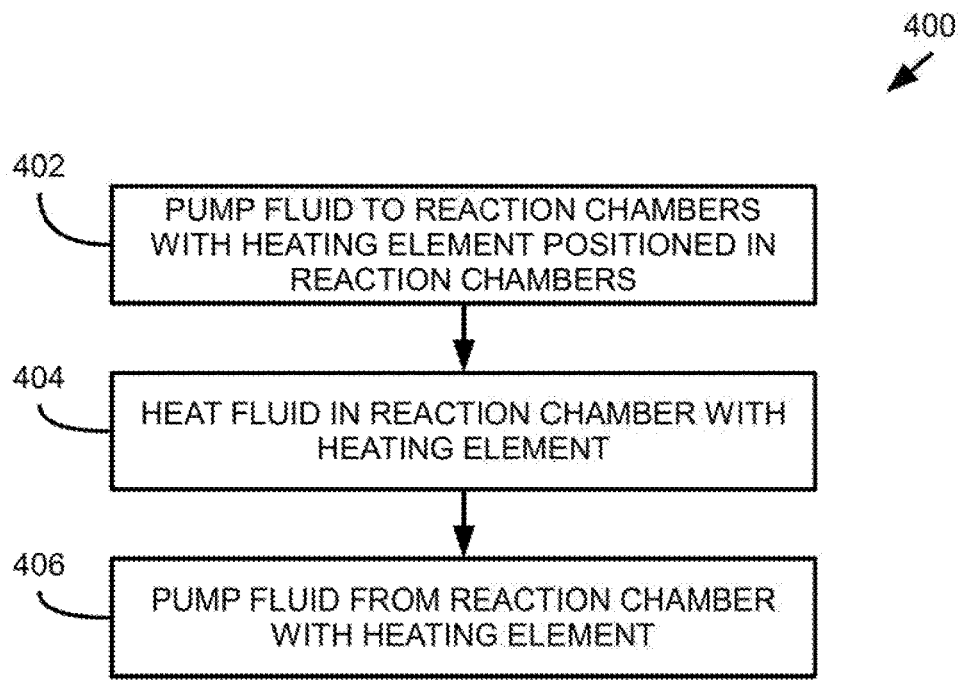

FIG. 8 provides a flowchart that illustrates a sequence of operations that may be performed by an example polymerase chain reaction device.

Figure 9:
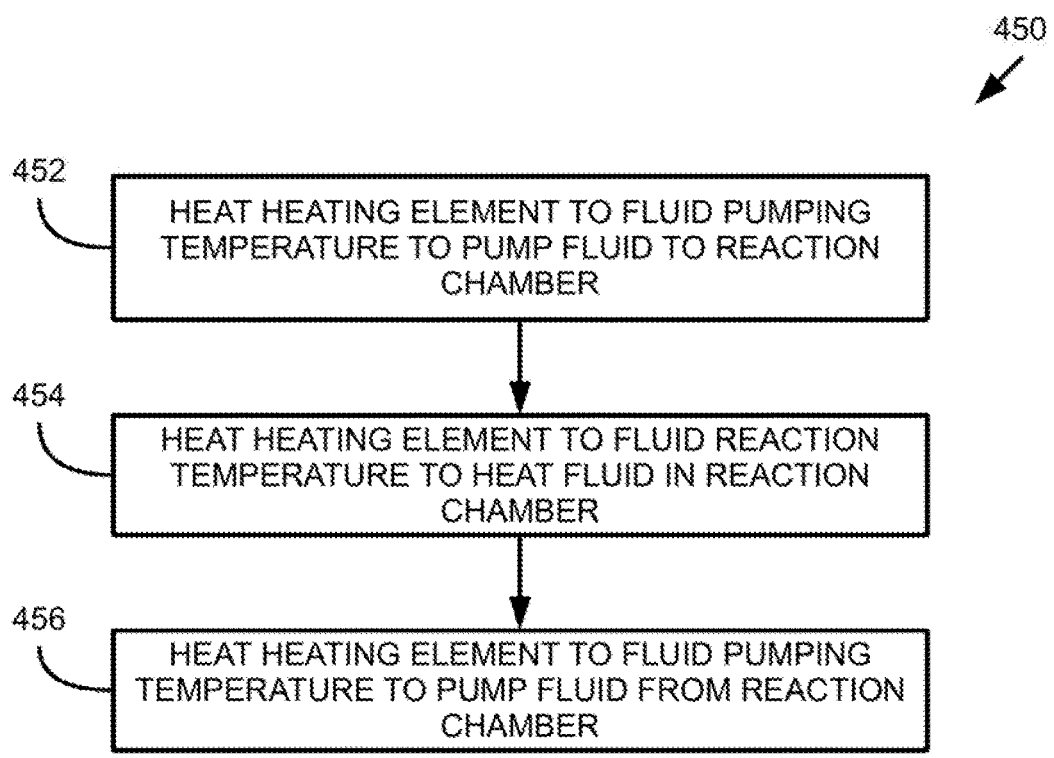

FIG. 9 provides a flowchart that illustrates a sequence of operations that may be performed by an example polymerase chain reaction device.

Figure 10:
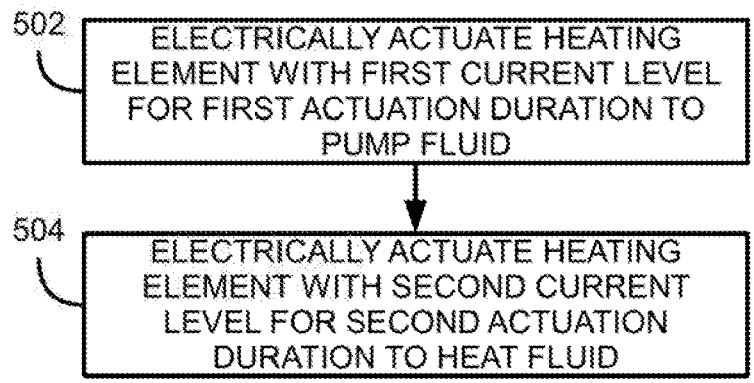

FIG. 10 provides a flowchart that illustrates a sequence of operations that may be performed by an example polymerase chain reaction device.

FIGS. 11A-D provide a block diagram that illustrates operation of some components of an example polymerase chain reaction device.

Throughout the drawings, identical reference numbers designate similar, but not necessarily identical, elements. The figures are not necessarily to scale, and the size of some parts may be exaggerated to more clearly illustrate the example shown. Moreover the drawings provide examples and/or implementations consistent with the description; however, the description is not limited to the examples and/or implementations provided in the drawings.

DESCRIPTION

Examples provided herein include devices, methods, and processes for polymerase chain reaction (PCR) processing. Some examples include polymerase chain reaction devices that comprise a fluid input, a fluid output, a set of microfluidic channels, and at least one heating element. In such examples, the set of microfluidic channels fluidly connect the fluid input and the fluid output. As will be appreciated, in some examples, the set of microfluidic channels may refer to a plurality of microfluidic channels that may be concurrently operated. Furthermore each microfluidic channel of the set comprises a reaction chamber. At least one heating element is positioned in each reaction chamber. The at least one heating element may heat fluid in the reaction chamber of each fluid channel. Furthermore, the at least one heating element may pump fluid to the reaction chamber and pump fluid from the reaction chamber of each microfluidic channel.

A polymerase chain reaction process facilitates amplification replication) of a target DNA molecule by causing performance of a denaturing reaction, an annealing reaction, and an extension reaction in a PCR mixture that includes the target DNA molecule, where the reactions may be repeated. A denaturing reaction corresponds to separation of the double helix structure of the target DNA molecule to create single stands of the target DNA molecule. An annealing reaction facilitates binding of primers included in the PCR mixture with corresponding parts of the single strands of the target DNA molecule. An extension reaction includes binding of polymerase to the primer and synthesizes a new DNA strand that is complementary to the DNA template strand. Example devices described herein may be used to perform a PCR process by electrically actuating a heating element in a reaction, chamber to cause at least one reaction of the PCR process.

In some examples described herein, a PCR mixture corresponding to a fluid may be pumped to a reaction chamber of each microfluidic channel with the at least one heating element. In some examples, a fluid may be a liquid. In some examples a fluid may be a gas. The PCR mixture in the reaction chamber may be heated for amplification of a DNA template included in the PCR mixture with the at least one heating element, and the PCR mixture may be pumped from the reaction chamber of each microfluidic channel with the at least one heating element. Therefore, as will be appreciated, examples described herein may comprise at least one heating element that may be used for heating of fluid and pumping of fluid to reaction chambers and from reaction chambers. In particular, in some examples, the at least one heating element may be heated to a fluid pumping temperature to thereby cause pumping of fluid to the reaction chamber and/or from the reaction chamber. To heat fluid for an operation associated with a polymerase chain reaction, the at least one heating element may be heated to a fluid reaction temperature.

For operations corresponding to a polymerase chain reaction process, example devices may heat fluid to various temperatures. For example, a heating element of a reaction chamber may be heated to a fluid reaction temperature to heat a volume of PCR mixture in the reaction chamber to a temperature of approximately 94° C. to approximately 96° C. such that a denaturation reaction may occur in the PCR mixture in the reaction chamber. As another example, a heating element of a reaction chamber may be heated to a fluid reaction temperature to heat a volume of PCR mixture in the reaction chamber to approximately 55° C. to approximately 60° C. such that an annealing reaction may occur in the PCR mixture in the reaction chamber. In another example, a heating element of a reaction chamber may be heated to a fluid reaction temperature to heat a volume of PCR mixture to a temperature of approximately 75° C. to approximately 80° C. such that and an extension reaction may occur in the PCR mixture in the reaction chamber. The term "approximately" when used with regard to a value may correspond to a range of ±10%.

Other examples may implement a two-step thermal cycling process. In such examples, a PCR mixture may be cycled between a first temperature of approximately 55° C. to approximately 60° C. and a second temperature of approximately 85° C. to approximately 90° C. In such examples, the extension and anneal operations may occur at the first temperature and the denaturation operation may occur at the second temperature. As will be appreciated, examples that implement the two-step thermal cycling process may perform replication/amplification in less time as compared to the three operation process described above.

To pump fluid to a reaction chamber and from a reaction chamber, examples may heat a heating element to a fluid pumping temperature, where a fluid pumping temperature may correspond to a temperature at which a bubble may form in fluid proximate the heating element. Formation and subsequent collapse of such bubble may cause jetting (i.e., flow) of the fluid. In some examples, a fluid pumping temperature may correspond to a temperature of the heating element that may cause fluid proximate the heating element to be heated to approximately 200° C. to approximately 300° C. Heating a heating element of a reaction chamber may be performed by electrically actuating the heating element. For example, if the heating element is a resistive component, the heating element may be heated by electrical actuation of a particular current level. In examples described herein, a fluid pumping temperature is relatively greater than a fluid reaction temperature.

Different levels of electrical actuation and a duration of such electrical actuation may correspond to pumping of fluid by a heating element or heating of a fluid for a PCR process by the heating element. In particular, in some examples, fluid may be pumped by a heating element positioned in a reaction chamber by rapidly heating the heating element to the fluid pumping temperature to cause formation and collapse of a bubble in fluid to be pumped. In such examples, the heating element may be electrically actuated with a first current level to cause pumping of fluid with the heating element, and the heating element may be electrically actuated with second current level to cause heating of fluid for a PCR process. In some example devices, the first current level is greater than the second current level. Similarly, a duration of the electrical actuation of the heating element with the first current level may be shorter as compared to electrical actuation of the heating element with the second current level for the PCR process. For example, for pumping of fluid, the heating element may be electrically actuated at a first current level for an actuation duration of approximately 0.001 milliseconds (mS), where the electrical actuation may be repeated at a frequency in the kilohertz scale. For heating of fluid for the PCR process, the heating element may be electrically actuated at a second current level for an actuation duration of approximately 10-100 mS for a denaturation reaction, approximately 0.5 to approximately 10 seconds for an extension or anneal reaction.

Examples described herein include polymerase chain reaction devices that may be lab-on-a-chip implementations. In such examples, a polymerase chain reaction device may comprise a substrate into which microfluidic channels may be formed. The substrate may comprise a silicon based wafer or other such similar materials used for microfabricated devices (e.g., glass, gallium arsenide, plastics, etc). Furthermore, the at least one heating element may be a resistor component (which may be referred to as simply a "resistor"), such as a thin-film resistor. Accordingly, in some examples, the at least one heating element may be formed on the substrate, where at least a portion of the heating element is positioned in each reaction chamber of each microfluidic channel.

Example PCR devices described herein may comprise a plurality of microfluidic channels in a respective set. Each microfluidic channel may include at least one reaction chamber. In some examples, each microfluidic channel may include more than one reaction chamber. Some example PCR devices may comprise reaction chambers that each have a reaction chamber volume such that the reaction chamber is sized to process a single DNA template molecule for a PCR process. For example, the reaction chambers of each microfluidic channel may have a reaction chamber volume within a range of approximately 1 picoliter (pL) to approximately 1 nanoliter (nL). In some examples, the reaction chamber volume may be such that a relatively low number of DNA template molecules (i.e., approximately 2 molecules to approximately 50 molecules) may be processed in each reaction chamber. In examples in which a single DNA template molecule may be processed and replicated with each reaction chamber, the polymerase chain reaction device may be implemented in a digital polymerase chain reaction (dPCR) process. Accordingly, such examples may be referred to as digital polymerase chain reaction devices. As will be appreciated, in an example dPCR device implemented in a dPCR process, some reaction volumes may process a single DNA template molecule, while some reaction volumes may not contain a DNA template molecule. In such examples, the absence of DNA template molecules in some reaction chambers (due in part to the volume of the reaction chambers) may facilitate quantification of the molecular sample of the PCR process.

Turning now to the figures, and particularly to FIG. 1, this figure provides a block diagram that illustrates some components of an example polymerase chain reaction device 10. In this example, the device 10 comprises a fluid input 12 and a fluid output 14. The device 10 comprises a set of microfluidic channels 16 fluidly connecting the fluid input 12 and the fluid output 14. Each microfluidic channel 16 includes a reaction chamber 18. In this example, a heating element 20 is positioned in each reaction chamber 18. The heating element 20 is illustrated in dashed line for clarity and to illustrate that, in this example, the heating element 20 is an elongated component in which a respective portion of the heating element 20 is positioned in each reaction chamber 18. In the example implementation illustrated in FIG. 1, it will be appreciated that using an elongated heating element 20 that is partially positioned in each reaction chamber 18 may simplify fabrication of the device 10.

Furthermore, in this particular example, each microfluidic channel 16 comprises a first channel portion 22a that fluidly connects the fluid inlet 12 and the reaction chamber 18, and each microfluidic channel 16 comprises a second channel portion 22b that fluidly connects the reaction chamber 18 and the fluid outlet 14. In this example, a length of the first channel portion 22a of each microfluidic channel 16 is less than a length of the second channel portion 22b. Accordingly, the reaction chambers 18 may be described as asymmetrically arranged relative to the fluid input 12 and fluid output 14. In examples similar to the example device 10 of FIG. 1, asymmetric arrangement of the reaction chambers relative to the fluid input and fluid output may facilitate pumping of fluid to and from such reaction chambers. While in the example provided in FIG. 1, the example device 10 is illustrated with three microfluidic channels 16, it will be appreciated that other examples may include more or less microfluidic channels 16. Moreover, while in this example, the length of the first channel portion 22a is illustrated as being relatively less than the length of the second channel portion 22b, it will be appreciated that other examples may have different arrangements.

During performance of a PCR process, the example device 10 of FIG. 1 may pump a PCR mixture in the form of fluid from the first channel portion 22a of each microfluidic channel to the reaction chamber 18. To pump the PCR mixture to the reaction chamber 18 of each microfluidic channel 16, the heating element 20 may be heated to a fluid pumping temperature. A volume of PCR mixture pumped to the reaction chamber 18 may be heated by the heating element 20 to a fluid reaction temperature to facilitate denaturing, annealing, and/or extension of a target DNA in the PCR mixture. After heating of the PCR mixture for a PCR related process, the PCR mixture may be pumped from the reaction chamber 18 to the second channel portion 22b by heating the heating element 20 to the fluid pumping temperature.

FIG. 2 provides a block diagram that illustrates some components of an example PCR device 50 that comprises a fluid input 52 and a fluid output 54. The device 50 further comprises a set of microfluidic channels 56 that fluidly connect the fluid input 52 and the fluid output 54. Each microfluidic channel 56 includes a reaction chamber 58. In this example, the device 50 comprises a respective heating element 60 for each reaction chamber 58. Accordingly, as compared to the example device 10 of FIG. 1, which implements an elongated heating element 20 that is partially positioned in each reaction chamber 18, the example device 50 of FIG. 2 implements individual heating elements 60. As discussed previously, for each microfluidic channel 56, the respective heating element 60 may pump fluid to the reaction chamber 58. The respective heating element 60 may pump fluid from the reaction chamber 58. In addition, the respective heating element 60 may heat fluid in the reaction chamber 58. As will be appreciated, heating of fluid in the reaction chamber 58 may be performed for a PCR process.

FIG. 3 provides a block diagram that illustrates some components of an example PCR device 100. In this example, the device 100 comprises a fluid input 102 and a fluid output 104. The device further comprises a first set of microfluidic channels 106 and a second set of microfluidic channels 108. Each microfluidic channel 106, 108 comprises a reaction chamber 110. Furthermore, the device 100 comprises a first heating element 112 that is positioned in the reaction chamber 110 of each microfluidic channel of the first set 106, and the device 100 comprises a second heating element 114 that is positioned in the reaction chamber 110 of each microfluidic channel of the second set 108. In this example, the first heating element 112 and the second heating element 114 are illustrated in dashed line for clarity. As shown, the first and second heating elements 112, 114 are elongated heating elements. For the first heating element 112, a respective portion is positioned in the reaction chamber 110 of each microfluidic channel of the first set 106. Similarly, a respective portion of the second heating element 114 is positioned in the reaction chamber 110 of each microfluidic channel of the second set 108. While in this example, an elongated heating element overlaps each reaction chamber of a set of microfluidic channels, it will be appreciated that in other examples more than one elongated heating element may implemented for a reaction chambers of a set of microfluidic channels.

In this example, the reaction chambers 110 of the first set of microfluidic channels 106 are located proximate the fluid input 102, and the reaction chambers of the second set of microfluidic channels 108 are located proximate the fluid output 104 such that the reaction chambers 110 of the first set of microfluidic channels 106 and the reaction chambers 110 of the second set of microfluidic channels 108 are arranged in an interdigitated manner. The example interdigitated manner of FIG. 3 may be implemented to facilitate a compact layout for a polymerase chain reaction device and improved utilization of substrate area.

FIG. 4 provides a block diagram that illustrates some components of an example polymerase chain reaction device 150. The device 150 comprises a fluid input 152 and a fluid output 154. In addition, the device comprises a set of microfluidic channels 156 fluidly connecting the fluid input 152 and the fluid output 154. In this example, each microfluidic channel comprises a first reaction chamber 158 and a second reaction chamber 160. Furthermore, the device 150 comprises a heating element 162 positioned in each reaction chamber 158, 160. Each microfluidic channel 156 comprises a first channel portion 164a, a second channel portion 164b, and a third channel portion 164c. For each microfluidic channel 156, the first channel portion 164a fluidly connects the fluid input 152 and the first reaction chamber 158; the second channel portion 164b fluidly connects the first reaction chamber 158 and the second reaction chamber 160; and the third channel portion 164c fluidly connects the second reaction chamber 160 and the fluid output 154.

As shown in the example of FIG. 4, the first reaction chamber 158 is positioned proximate the fluid input 152, and the second reaction chamber 160 is positioned proximate the fluid output 154. Hence, a length of the first channel portion 164a and a length of the third channel portion 164c of each microfluidic channel 156 are less than a length of the second channel portion 164b. Therefore, the first reaction chamber 158 and the second reaction chamber 160 of each microfluidic channel 156 are arranged asymmetrically relative to the fluid input 152 and the fluid output 154.

In this example, a PCR mixture in the form of a fluid volume may be pumped to the first reaction chamber 158 of each microfluidic channel 156 from the first channel portion 164a by heating of the heating elements 162 of the first reaction chambers 158 and/or the heating elements 162 of the second reaction chambers 160 to a fluid pumping temperature. At least one operation of a PCR process may be performed for the PCR mixture in the first reaction chamber 158 by heating the heating element 162 to particular fluid reaction temperatures. For example, denaturation, annealing, and/or extension may be performed for the PCR mixture in the first reaction chamber 158. The PCR mixture may be pumped from the first reaction chamber 158 of each microfluidic channel 156 to the second channel portion 164b by heating the heating elements 162 of the first reaction chambers 158 and/or the heating elements 162 of the second reaction chambers 160 to a fluid pumping temperature.

The PCR mixture may be pumped from the second channel portion 164b to the second reaction chamber of each microfluidic channel 156 by heating the heating element elements 162 of the first reaction chambers 158 and/or the heating elements 162 of the second reaction chambers 160 to a fluid pumping temperature. One or more operations of a PCR process may be performed for the PCR mixture in the second reaction chamber 160 of each microfluidic channel 156 by heating the heating element 162 to particular fluid reaction temperatures. For example, denaturation, annealing, and/or extension may be performed on the PCR mixture in the second reaction chamber 160. The PCR mixture in the second reaction chamber 160 of each microfluidic channel 156 may be pumped to the third channel portion 164c of each microfluidic channel by heating the heating elements 162 of the second reaction chambers 160 to a fluid pumping temperature.

FIG. 5 provides a block diagram that illustrates some components of an example polymerase chain reaction device 200. As shown, the device 200 comprises a fluid input 202 and a fluid output 204. The device 200 further comprises a first set of microfluidic channels 206 and a second set of microfluidic channels 208 that fluidly connect the fluid input 202 and the fluid output 204. Each microfluidic channel 206, 206 comprises a first reaction chamber 210, a second reaction chamber 212, and a third reaction chamber 214. In addition, the device 200 comprises a heating element 216 in each reaction chamber 210-214. Similar to other examples described herein, the reaction chambers 210-214 of the first set of microfluidic channels 206 and the reaction chambers 210-214 of the second set of microfluidic channels 208 are arranged in an interdigitated manner between the fluid input 202 and the fluid output 204. Moreover the reaction chambers 210-214 of the first set of microfluidic channels 206 and the reaction chambers 210-214 of the second set of microfluidic channels 208 are arranged asymmetrically relative to the fluid input 202 and the fluid output 204—i.e., the reaction chambers 210-214 are not evenly spaced between the fluid input 202 and the fluid output 204.

FIG. 6 is a block diagram that illustrates some components of an example polymerase chain reaction device 250. The example device 250 of FIG. 6 comprises a fluid input 252, a fluid output 254, and a set of microfluidic channels 256 that fluidly connect the fluid input 252 and the fluid output 254. Each microfluidic channel 256 comprises a reaction chamber 258, and the device 250 comprises a heating element 260 positioned in each reaction chamber 258. Furthermore, in this example, the device 250 comprises an inertial pump 262 positioned in each microfluidic channel 256. The inertial pump 262 in each microfluidic channel 256 may pump fluid to the reaction chamber 258. As discussed previously, the heating element 260 of each reaction chamber 258 may also be used to pump fluid. Hence in examples similar to the example of FIG. 6, fluid pumping may be performed with the inertial pumps 262 and/or the heating elements 260.

Inertial pumps 262 may comprise fluid actuators that may generate compressive and tensile fluid displacements to thereby cause fluid flow (i.e., movement). As will be appreciated, an inertial pump may be connected to a controller, and electrical actuation of an inertial pump by the controller may thereby control pumping of fluid. Fluid actuators that may be implemented in inertial pumps described herein may include, for example, thermal resistor based actuators, piezo-membrane based actuators, electrostatic membrane actuators, mechanical/impact driven membrane actuators, magneto-strictive drive actuators, and/or other such microdevices.

FIG. 7 provides a block diagram that illustrates some components of an example polymerase chain reaction device 300. Example polymerase chain reaction devices may be microfabricated devices, where some components and features of the device may be at least partially formed on a substrate by various microfabrication processes. The example device 300 of FIG. 7 comprises a substrate 302 upon which some components of the device are coupled and/or formed. As shown, the device 300 may comprise a controller 304 and a machine readable memory 306 coupled to the substrate 302. The machine-readable memory 306 includes instructions 308 that may be executed by the controller 304.

While the term "controller" may be used herein, it will be appreciated that a controller may comprise various types of data processing resources. A controller may include, for example, at least one hardware based processor. Similarly, a controller may comprise one or more general purpose data processors and/or one or more specialized data processors. For example, a controller may comprise a central processing unit (CPU), an application-specific integrated circuit (ASIC), and/or other such configurations of logical components for data processing. Execution of the instructions 308 may cause the controller 304 and/or device 300 to perform the functionalities, processes, and/or sequences of operations described herein. Furthermore, in the examples, the machine-readable memory 306 may comprise a machine-readable storage medium, which may be referred to as a memory and/or a memory resource. The machine-readable memory may represent random access memory (RAM) devices as well as other types of memory (e.g. cache memories, non-volatile memory devices, read-only memories, etc.). A machine-readable storage medium may include RAM, ROM, erasable programmable read-only memory (EPROM), electrically erasable programmable read-only memory, flash memory or other solid state memory technology, or any other medium that may be used to store executable instructions and information. Furthermore, the machine-readable memory 306 may be non-transitory.

The device 300 further comprises a fluid input 310, a fluid output 312, and a set of microfluidic channels 314. As shown, the microfluidic channels 314 may be positioned between the fluid input 310 and the fluid output 312, and the microfluidic channels 314 fluidly connect the fluid input 310 and the fluid output 312. Each microfluidic channel 314 comprises a reaction chamber 316, where each reaction chamber 316 is positioned asymmetrically relative to the fluid input 310 and fluid output 312. Furthermore, the example device 300 comprises a heating element 318 positioned in each reaction chamber 316. In addition, the example device 300 comprises a temperature sensor 320 positioned in each reaction chamber. As shown, the controller 304 may be connected to the heating elements 318 and/or the temperature sensors 320. In this example, the fluid input 310, fluid output 312, and/or microfluidic channels 314 may be features at least partially formed in the substrate 302.

In this example, instructions 308 may be executable by the controller 304, and execution of the instructions 308 by the controller 304 may cause the controller 304 to electrically actuate the heating elements 318. In such examples, the controller 304 may receive temperature data from the temperature sensors 320 which may facilitate feedback for electrical actuation of the heating elements 318. In particular, execution of some instructions 308 may cause the controller to electrically actuate the heating elements 318 to thereby cause the heating elements 318 to pump fluid to/from the respective reaction chambers 316. In addition, execution of some instructions 308 may cause the heating elements 318 to heat fluid in the respective reaction chambers 316 for an operation associated with a PCR process. For example, if the heating elements 318 are resistive components, the controller 304 may electrically actuate the heating elements 318 with a first current level such that the heating elements 318 are heated to a fluid pumping temperature. Similarly, the controller may electrically actuate the heating elements 318 with a second current level such that the heating elements 318 are heated to a fluid reaction temperature.

FIGS. 8-10 provide flowcharts that provide example sequences of operations that may be performed by an example polymerase chain reaction device to perform example processes and methods as described herein. In some examples, some operations included in the flowcharts may be embodied in a memory (such as the machine-readable memory 306 of FIG. 7) in the form of instructions that may be executable by a controller to cause a device to perform the operations corresponding to the instructions. Additionally, the examples provided in FIGS. 8-10 may be embodied in processes and/or methods. In some examples, the example processes and/or methods disclosed in the flowcharts of FIGS. 8-10 may be performed by a controller implemented in a device, such as the example controller of FIG. 7.

Turning now to FIG. 8, this figure provides a flowchart 400 that illustrates an example sequence of operations that may be performed by an example PCR device. The example PCR device may comprise a fluid input, a fluid output, and a set of microfluidic channels that fluidly connect the fluid input and the fluid output. In addition, each microfluidic channel may comprise a reaction chamber, and the example device may comprise at least one heating element positioned in the reaction chambers. In this example, a PCR device may pump fluid to each reaction chamber of each microfluidic channel with the at least one heating element (block 402). The example device may heat fluid in each reaction chamber with the at least one heating element (block 404), and the device may pump fluid from the reaction chamber with the heating element (block 406).

FIG. 9 provides a flowchart 450 that illustrates an example sequence of operations that may be performed by an example PCR device. In this example, the PCR device may comprise microfluidic channels, where each microfluidic channel comprises a reaction chamber. Furthermore, the device comprises at least one heating element that is positioned in each reaction chamber. The example device may heat the at least one heating element to a fluid pumping temperature to thereby pump fluid to the reaction chamber (block 452). The heating element may be heated to a fluid reaction temperature to thereby heat fluid in the reaction chamber of each microfluidic channel (block 454). The heating element may then be heated to the fluid pumping temperature to thereby pump fluid from the reaction chamber (block 456).

FIG. 10 provides a flowchart 500 that illustrates an example sequence of operations that may be performed by an example PCR device. In this example, the device may comprise a set of microfluidic channels, where each microfluidic channel comprises a reaction chamber. Furthermore, the device comprises at least one heating element positioned in each reaction chamber, and the device comprises a controller connected to the at least one heating element. The device may electrically actuate the at least one heating element with a first current level for a first actuation duration to pump fluid to each reaction chamber and/or from each reaction chamber (block 502). As discussed previously, to pump fluid, a heating element may be rapidly heated to a fluid pumping temperature for a short duration to thereby cause bubble formation and collapse (which may be referred to as jetting) in fluid that causes flow in the fluid. Accordingly, the first current level corresponds to the fluid pumping temperature and the first actuation duration corresponds to the length of time that the first current level is applied to the at least one heating element to cause pumping of fluid.

Furthermore, the device may electrically actuate the at least one heating element with a second current level for a second actuation duration to heat fluid in the reaction chambers (block 504). As discussed, to heat fluid for a PCR process, a heating element may be heated to a fluid reaction temperature. In such examples, the second current level corresponds to the fluid reaction temperature and the second actuation duration corresponds to the length of time that the second current level is applied to the at least one heating element to heat fluid for a PCR process. In some examples, the first current level is greater than the second current level, and the first actuation duration is less than the second actuation duration.

FIGS. 11A-D provide block diagrams that illustrate operation of some components of an example polymerase chain reaction device 550. The example provided in FIGS. 11A-D illustrates pumping and heating of a volume of fluid in a microfluidic channel 552 that comprises a reaction chamber 554. In FIGS. 11A-D, fluid may be pumped and heated by a heating element 556 positioned in the reaction chamber. In FIG. 11A, a volume of fluid 558 may be pumped from a first channel portion 560 of the microfluidic channel 552 to the reaction chamber 554 by operation of the heating element 556 as described herein. In FIG. 11B, the volume of fluid 558 may be heated in the reaction chamber 554 by the heating element 556 for an operation of the PCR process. In FIG. 11C, the volume of fluid 558 may be pumped from the reaction chamber 554 to a second channel portion 562 of the microfluidic channel 552 by the heating element 556 as described herein. In FIG. 11D, the volume of fluid 558 has been pumped to the second channel portion 562, and another volume of fluid 564 may be in the first channel portion 560 for pumping into the reaction chamber 554.

As will be appreciated, the operations described above with respect to the flowcharts and example PCR devices may be performed during performance of a PCR process. As such, the fluid may correspond to a PCR mixture, and heating of fluid may correspond to denaturing, annealing, and/or extension operations associated with a PCR process. Furthermore, PCR devices as described herein may be implemented in analysis systems. For example, fluid outputs of the various examples described herein may be further connected to analysis and/or detection components.

Accordingly, the examples described herein provide examples of a polymerase chain reaction device in which at least one heating element may be implemented and used to perform two operations. In particular, the at least one heating element may be used to pump fluid in example devices, and the at least one heating element may be used to heat fluid for operations associated with a polymerase chain reaction. Implementation of such dual use heating element in PCR devices may facilitate reduction of components as compared to other types of PCR devices. Moreover, utilization of a heating element for pumping of fluid and heating thereof may facilitate reduction of device size and simplification of electrical connection layouts in such devices. In addition, example devices as described herein may facilitate manipulation of small volumes of fluid (e.g., approximately 1 nL to approximately 1 pL.) Because examples described herein facilitate pumping and heating of such small volumes of fluid (such as small volumes of PCR mixtures), examples described herein may facilitate digital polymerase chain reaction processing of fluid samples.

The preceding description has been presented to illustrate and describe examples of the principles described. This description is not intended to be exhaustive or to limit these principles to any precise form disclosed. Many modifications and variations are possible in light of the above disclosure.

The invention claimed is:

1. A polymerase chain reaction device comprising:
   a fluid input;
   a fluid output;
   a set of microfluidic channels fluidly connected to the fluid input and the fluid output, each microfluidic channel of the set comprising a reaction chamber, the set of microfluidic channels being non-intersecting;

at least one heating element, the at least one heating element positioned in the reaction chamber of each microfluidic channel, the at least one heating element configured to both:
    heat fluid in the reaction chamber of each of the microfluidic channels by heating to a fluid reaction temperature, and
    pump the fluid to the reaction chamber and from the reaction chamber of each of the microfluidic channels by heating to a fluid pumping temperature, the fluid pumping temperature being greater than the fluid reaction temperature; and
a controller connected to the at least one heating element, the controller configured to:
    electrically actuate the at least one heating element with a first current level to cause the heating element to heat to the fluid pumping temperature to pump the fluid to the reaction chamber and from the reaction chamber;
    electrically actuate the at least one heating element with a second current level to cause the at least one heating element to heat to the fluid reaction temperature to heat the fluid in the reaction chamber of each of the microfluidic channels.

2. The device of claim 1, wherein each of the microfluidic channels comprises a first channel portion fluidly connecting the fluid input and the reaction chamber thereof, each of the microfluidic channels further comprising a second channel portion fluidly connecting the reaction chamber and the fluid output, and the at least one heating element is further configured to, via the controller controlling a current thereof, pump the fluid to the reaction chamber from the first channel portion; and pump the fluid from the reaction chamber to the second channel portion.

3. The device of claim 2, wherein the first channel portion is of a first length, the second channel portion is of a second length, and the first length and the second length are not equal, such that the reaction chamber of each of the microfluidic channels is arranged asymmetrically relative to the fluid input and the fluid output.

4. The device of claim 1, wherein the at least one heating element comprises a single elongated heating element that is partially positioned in each reaction chamber.

5. The device of claim 1, wherein the at least one heating element comprises a respective heating element for each reaction chamber.

6. The device of claim 1, wherein each reaction chamber has a reaction chamber volume within a range of approximately 1 picoliter to 1 nanoliter.

7. The device of claim 1, wherein the set of microfluidic channels comprises a first set of microfluidic channels, and the device further comprises:
a second set of microfluidic channels fluidly connected to the fluid input and the fluid output, each microfluidic channel of the second set comprising a reaction chamber, the first set and the second set of microfluidic channels being non-intersecting,
wherein the reaction chambers of the first set of microfluidic channels are positioned proximate the fluid input and the reaction chambers of the second set of microfluidic channels are positioned proximate the fluid output such that the reaction chambers of the first set of microfluidic channels and the reaction chambers of the second set of microfluidic channels are arranged in an interdigitated manner.

8. The device of claim 1, wherein the reaction chambers of each of the microfluidic channels of the set is a first reaction chamber, the at least one heating element is a first at least one heating element, each of the microfluidic channels further comprises a second reaction chamber, and the device further comprises:
a second at least one heating element positioned in the second reaction chamber of each of the microfluidic channels, the second at least one heating element to, via the controller controlling a current thereof:
    heat the fluid in the second reaction chamber of each microfluidic channel of the set, and
    pump the fluid to the second reaction chamber and from the second reaction chamber of each microfluidic channel of the set.

9. The device of claim 1, further comprising:
an inertial pump associated with each of microfluidic channels, each inertial pump including a fluid actuator to pump the fluid in the microfluidic channels,
wherein the microfluidic channels are formed in a substrate and the at least one heating element comprises a thin-film resistor formed on the substrate.

10. The device of claim 1, further comprising a digital polymerase chain reaction device, and each reaction chamber of the set of the microfluidic channels has a reaction chamber volume such that the reaction chamber is sized to process a single DNA template molecule.

11. A method comprising:
providing a polymerase chain reaction device comprising:
    a set of microfluidic channels, each of the microfluidic channels of the set comprising a reaction chamber, the set of the microfluidic channels being non-intersecting, at least one heating element positioned in the reaction chamber of each of the microfluidic channels; and a controller;
    electrically actuating, via the controller, the at least one heating element with a second current level to cause the at least one heating element to heat to a fluid pumping temperature to pump a fluid to the reaction chamber of each of the microfluidic channels;
electrically actuating, via the controller, the at least one heating element with a first current level to cause the at least one heating element to heat to a fluid reaction temperature to heat the fluid in the reaction chamber of each of the microfluidic channels, the fluid pumping temperature being greater than the fluid reaction temperature; and
electrical actuating, via the controller the at least one heating element with the second current level to cause the at least one heating element to heat to the fluid pumping temperature to pump the fluid from the reaction chamber each of the microfluidic channels.

12. A polymerase chain reaction device, comprising:
a fluid input;
a fluid output;
a set of microfluidic channels fluidly connecting the fluid input and the fluid output, each microfluidic channel comprising an asymmetrically arranged reaction chamber, the set of microfluidic channels being non-intersecting;
at least one heating element positioned in each reaction chamber, the heating element configured to both:
    pump fluid to the reaction chamber and from the reaction chamber of each of the microfluidic channels by thermal actuation with the heating element by heating to a fluid pumping temperature, and
    heat the fluid in the reaction chamber of each of the microfluidic channels by heating to a fluid reaction temperature, the fluid pumping temperature being greater than the fluid reaction temperature, and a controller connected to the at least one heating element, the controller configured to:

electrically actuate the at least one heating element with a first current level to cause the heating element to heat to the fluid pumping temperature to pump the fluid to the reaction chamber and from the reaction chamber, and electrically actuate the at least one heating element with a second current level to cause the heating element to heat to the fluid reaction temperature to heat the fluid in the reaction chamber of each microfluidic channel.

* * * * *